United States Patent [19]

Harris et al.

[11] Patent Number: 5,618,543

[45] Date of Patent: Apr. 8, 1997

[54] COMPOSITION AND METHOD FOR REDUCING SNORING AND RESPIRATORY PROBLEMS

[76] Inventors: Dennis H. Harris, 531 E. McDowell, Phoenix, Ariz. 85004; Ronald E. General, 30 N. 56th St., Phoenix, Ariz. 85034

[21] Appl. No.: 512,460

[22] Filed: Aug. 8, 1995

[51] Int. Cl.$^6$ ............................ A61K 38/16; A61K 38/43
[52] U.S. Cl. .................... 424/400; 424/439; 424/451; 424/464; 424/94.2
[58] Field of Search ................... 424/400, 439, 424/451, 464, 94.2

[56] References Cited

U.S. PATENT DOCUMENTS

| | | |
|---|---|---|
| 180,303 | 7/1896 | Woods . |
| 3,493,652 | 2/1970 | Hartman . |
| 4,079,125 | 3/1978 | Sipos . |
| 4,556,557 | 12/1985 | Reichert . |
| 4,668,513 | 5/1987 | Reichert . |
| 4,876,283 | 10/1989 | Reichert . |
| 5,082,665 | 1/1992 | Verny . |
| 5,436,003 | 7/1995 | Rohde, Jr. et al. . |
| 5,489,572 | 2/1996 | Yoshida et al. ............... 504/320 |

OTHER PUBLICATIONS

Panciera et al., "Acute oxalate poisoning attributable to ingestion of curly dock (Rumex Crispus) in sheep", Medline abstract#90307531, Journal of the American Veterinary Medical Association (Jun. 1990).
Protiva, CA 111:133,991, abstract of Czech Patent 236339 (1–88).

*Primary Examiner*—Jeffrey Mullis
*Attorney, Agent, or Firm*—LaValle D. Ptak

[57] ABSTRACT

A composition for reducing snoring and reducing allergy and sinus symptoms uses natural enzymes and herbs. The enzymes include protease, amylase, lipase and cellulase combined with acerola and yellowdock in a natural fiber base, preferably made of beet plant fiber. The formula preferably is administered in capsules or tablets, with doses administered according to the weight of the user.

19 Claims, No Drawings

COMPOSITION AND METHOD FOR REDUCING SNORING AND RESPIRATORY PROBLEMS

BACKGROUND

In the United States, it is estimated that approximately forty percent of the population is afflicted with snoring problems of sufficient severity to disturb the sleep of the person doing the snoring, or the mate of such a person, on a regular basis. Snoring is caused, in general, by an interference with the passage of air through the upper respiratory system. This may be due to airway congestion from drainage, from allergies, or from mechanical obstruction. Whatever the cause, the noise produced is highly undesirable.

In the past, therapy for eliminating or reducing snoring has included the administration of decongestants and antihistamines, which generally have been ineffective. Such medications have exhibited, at best, limited success for reducing drainage due to colds, allergies and the like.

Another approach to eliminating or reducing snoring is to employ surgical techniques. Primary among these techniques are partial uvulectomies, which have achieved limited success. Surgical procedures, whether utilizing a surgical knife to affect procedure or, more recently, employing laser surgical techniques, result in considerable discomfort following the procedure. As with any invasive surgical procedure, there is a risk of infection, bleeding and possible adverse reaction to anesthesia. Even where a partial uvulectomy has been effected, limited success at solving the problem of snoring occurs.

A third technique for reducing or eliminating snoring includes the use of mechanical appliances, which are externally applied to the nose or nasal passages in the nose. Such mechanical appliances include a reverse spring which is externally mounted on the nose to hold the nostrils wide open, thereby, at least theoretically, increasing the size of the air passage while the person, on which the device is mounted, is sleeping. Of course such a mechanical treatment has no effect whatsoever for snoring which takes place when a person breathes through his or her mouth.

Accordingly, it is desirable to provide a simple, easy to use, relatively inexpensive, and effective procedure for substantially reducing or eliminating problem snoring.

SUMMARY OF THE INVENTION

It is an object of this invention to provide an improved composition for reducing snoring.

It is an additional object of this invention to provide an improved natural remedy for reducing snoring.

It is another object of this invention to provide an improved composition utilizing enzymes and herbs for reducing snoring.

It is a further object of this invention to provide an improved, orally administered tablet or capsule, which effectively reduces snoring.

In accordance with a preferred embodiment of this invention, a composition for reducing snoring and alleviating respiratory problems is comprised of protease, amylase, lipase and cellulase combined with acerola and yellowdock in a natural fiber carrier.

DETAILED DESCRIPTION

In accordance with a preferred embodiment of this invention, a composition for reducing snoring is made of a combination of natural herbs and enzymes. The herbs and enzymes preferably are combined in a tablet or capsule with a natural fiber carrier, or are placed in a liquid base for oral administration or administration in a spray or mist form.

In formulating various compositions suitable for reducing snoring, enzymes of protease, amylase, lipase and cellulase were combined with acerola and yellowdock in a natural fiber base (preferably beet plant fiber) and formed into tablets or capsules, generally the size of commercially available aspirin tablets and capsules for adult use. Various formulations of these ingredients were tested over a two year period. All of the subjects participating in the test were individuals known to be moderate to severe snorers for at least five years prior to the test, as verified by the person undergoing the test, or verified by a mate or member of the family of the person undergoing the test. Each formulation was tested on twenty subjects for six days. In some cases, different formulations were used on the same subjects in different tests. The results were graded as "poor", that is, less than 50% improvement; "good", that is snoring reduced by 50% to 75%; and "excellent", snoring reduced by 75% to 100%. All of the grading on these three levels was done by the test subject, the mate of the test subject, or family members of the test subject based on direct observation of the test subject.

During all of the tests, no cases of allergic or hypersensitivity reactions, side effects, or intolerance to the composition being used by the test subject was reported. All of the formulations used were administered orally in either a tablet or capsule form for the various tests; but the same formulations of active ingredients also may be placed in a suitable liquid carrier without affecting the results. The specific dosage used for each subject was based on weight. Up to 125 pounds, one tablet or capsule was administered. Between 125 pounds and 220 pounds, two tablets or capsules were administered; and over 220 pounds, three tablets or capsules were administered. All administration of the capsules or tablets was made between forty-five and sixty minutes before bedtime of the subject undergoing the test.

The following eleven examples, all using compositions of these herbs and enzymes in varying amounts formulated into tablets and capsules with a natural fiber base consisting of beet plant fiber, are provided, showing the actual test results. The amount which is listed for the composition in each of the examples is the amount for one tablet or capsule. This is the dosage for subjects with a weight of 125 pounds or less. For subjects in the higher weight ranges, two or three tablets or capsules, in accordance with the weight ranges given above, were administered.

EXAMPLE 1

| COMPOSITION | AMOUNTS |
| --- | --- |
| PROTEASE | 5,000 Hemoglobin Units (HU) |
| AMYLASE | 500 Dextrizing Units (DU) |
| LIPASE | 10 Lipase Units (LU) |
| CELLULASE | 50 Cellulase Units (CU) |
| ACEROLA | 25 Milligrams (mg) |
| YELLOWDOCK | 25 Milligrams (mg) |

Subjects

A total of twenty subjects were tested. The subjects included six women and fourteen men. The age range of the subjects was 24 years to 67 years; and the weight range was from 102 pounds to 205 pounds.

| Results | | |
|---|---|---|
| POOR - 30% | GOOD - 55% | EXCELLENT - 15% |

EXAMPLE 2

| COMPOSITION | AMOUNTS |
|---|---|
| PROTEASE | 20,000 Hemoglobin Units (HU) |
| AMYLASE | 10,000 Dextrizing Units (DU) |
| LIPASE | 800 Lipase Units (LU) |
| CELLULASE | 5,000 Cellulase Units (CU) |
| ACEROLA | 100 Milligrams (mg) |
| YELLOWDOCK | 150 Milligrams (mg) |

Subjects

A total of twenty subjects including four women and sixteen men were tested. The age range of the subjects was 18 years to 56 years; and the weight range was from 98 pounds to 240 pounds.

| Results | | |
|---|---|---|
| POOR - 15% | GOOD - 30% | EXCELLENT - 55% |

EXAMPLE 3

| COMPOSITION | AMOUNTS |
|---|---|
| PROTEASE | 40,000 Hemoglobin Units (HU) |
| AMYLASE | 20,000 Dextrizing Units (DU) |
| LIPASE | 1,600 Lipase Units (LU) |
| CELLULASE | 10,000 Cellulase Units (CU) |
| ACEROLA | 200 Milligrams (mg) |
| YELLOWDOCK | 250 Milligrams (mg) |

Subjects

A total of twenty subjects including nine women and eleven men were tested. The age range of the subjects was 18 years to 76 years; and the weight range was from 113 pounds to 209 pounds.

| Results | | |
|---|---|---|
| POOR - 10% | GOOD - 35% | EXCELLENT - 55% |

EXAMPLE 4

| COMPOSITION | AMOUNTS |
|---|---|
| PROTEASE | 5,000 Hemoglobin Units (HU) |
| AMYLASE | 2,000 Dextrizing Units (DU) |
| LIPASE | 40 Lipase Units (LU) |
| CELLULASE | 200 Cellulase Units (CU) |
| ACEROLA | 75 Milligrams (mg) |
| YELLOWDOCK | 100 Milligrams (mg) |

Subjects

A total of twenty subjects including ten women and ten men were tested. The age range of the subjects was 23 years to 62 years; and the weight range was from 106 pounds to 232 pounds.

| Results | | |
|---|---|---|
| POOR - 15% | GOOD - 30% | EXCELLENT - 55% |

EXAMPLE 5

| COMPOSITION | AMOUNTS |
|---|---|
| PROTEASE | 5,000 Hemoglobin Units (HU) |
| AMYLASE | 500 Dextrizing Units (DU) |
| LIPASE | 40 Lipase Units (LU) |
| CELLULASE | 200 Cellulase Units (CU) |
| ACEROLA | 75 Milligrams (mg) |
| YELLOWDOCK | 100 Milligrams (mg) |

Subjects

A total of twenty subjects including twelve women and eight men were tested. The age range of the subjects was 21 years to 58 years; and the weight range was from 122 pounds to 196 pounds.

| Results | | |
|---|---|---|
| POOR - 25% | GOOD - 60% | EXCELLENT - 15% |

EXAMPLE 6

| COMPOSITION | AMOUNTS |
|---|---|
| PROTEASE | 5,000 Hemoglobin Units (HU) |
| AMYLASE | 2,000 Dextrizing Units (DU) |
| LIPASE | 10 Lipase Units (LU) |
| CELLULASE | 200 Cellulase Units (CU) |
| ACEROLA | 75 Milligrams (mg) |
| YELLOWDOCK | 100 Milligrams (mg) |

Subjects

A total of twenty subjects including nine women and eleven men were tested. The age range of the subjects was 20 years to 60 years; and the weight range was from 110 pounds to 265 pounds.

| Results | | |
|---|---|---|
| POOR - 25% | GOOD - 65% | EXCELLENT - 10% |

EXAMPLE 7

| COMPOSITION | AMOUNTS |
|---|---|
| PROTEASE | 5,000 Hemoglobin Units (HU) |
| AMYLASE | 2,000 Dextrizing Units (DU) |
| LIPASE | 40 Lipase Units (LU) |
| CELLULASE | 50 Cellulase Units (CU) |

-continued

| COMPOSITION | AMOUNTS |
|---|---|
| ACEROLA | 75 Milligrams (mg) |
| YELLOWDOCK | 100 Milligrams (mg) |

Subjects

A total of twenty subjects including thirteen women and seven men were tested. The age range of the subjects was 18 years to 72 years; and the weight range was from 94 pounds to 202 pounds.

| Results | | |
|---|---|---|
| POOR - 25% | GOOD - 60% | EXCELLENT - 15% |

EXAMPLE 8

| COMPOSITION | AMOUNTS |
|---|---|
| PROTEASE | 5,000 Hemoglobin Units (HU) |
| AMYLASE | 2,000 Dextrizing Units (DU) |
| LIPASE | 40 Lipase Units (LU) |
| CELLULASE | 200 Cellulase Units (CU) |
| ACEROLA | 25 Milligrams (mg) |
| YELLOWDOCK | 100 Milligrams (mg) |

Subjects

A total of twenty subjects including five women and fifteen men were tested. The age range of the subjects was 26 years to 69 years; and the weight range was from 101 pounds to 214 pounds.

| Results | | |
|---|---|---|
| POOR - 30% | GOOD - 55% | EXCELLENT - 15% |

EXAMPLE 9

| COMPOSITION | AMOUNTS |
|---|---|
| PROTEASE | 5,000 Hemoglobin Units (HU) |
| AMYLASE | 2,000 Dextrizing Units (DU) |
| LIPASE | 40 Lipase Units (LU) |
| CELLULASE | 200 Cellulase Units (CU) |
| ACEROLA | 25 Milligrams (mg) |
| YELLOWDOCK | 25 Milligrams (mg) |

Subjects

A total of twenty subjects including nine women and eleven men were tested. The age range of the subjects was 18 years to 70 years; and the weight range was from 102 pounds to 202 pounds.

| Results | | |
|---|---|---|
| POOR - 30% | GOOD - 50% | EXCELLENT - 20% |

EXAMPLE 10

| COMPOSITION | AMOUNTS |
|---|---|
| PROTEASE | 5,000 Hemoglobin Units (HU) |
| AMYLASE | 2,000 Dextrizing Units (DU) |
| LIPASE | 40 Lipase Units (LU) |
| CELLULASE | 200 Cellulase Units (CU) |
| ACEROLA | 75 Milligrams (mg) |
| YELLOWDOCK | 75 Milligrams (mg) |

Subjects

A total of twenty subjects including ten women and ten men were tested. The age range of the subjects was 18 years to 67 years; and the weight range was from 110 pounds to 220 pounds.

| Results | | |
|---|---|---|
| POOR - 20% | GOOD - 60% | EXCELLENT - 20% |

EXAMPLE 11

| COMPOSITION | AMOUNTS |
|---|---|
| PROTEASE | 10,000 Hemoglobin Units (HU) |
| AMYLASE | 4,000 Dextrizing Units (DU) |
| LIPASE | 100 Lipase Units (LU) |
| CELLULASE | 400 Cellulase Units (CU) |
| ACEROLA | 100 Milligrams (mg) |
| YELLOWDOCK | 150 Milligrams (mg) |

Subjects

A total of twenty subjects including eight women and twelve men were tested. The age range of the subjects was 22 years to 65 years; and the weight range was from 116 pounds to 226 pounds.

| Results | | |
|---|---|---|
| POOR - 15% | GOOD - 30% | EXCELLENT - 55% |

As mentioned above, the administration of the composition was the same for all of the subjects in all of the different examples. For the formula of each example, the amounts shown are the amounts which were formulated into a single tablet or capsule. As mentioned previously, from one to three capsules or tablets were given to the various subjects, depending upon the weight of the subject in the three ranges discussed previously. For all of the formulations, the average results were poor-21.72%; good-47.96%; and excellent-30.32%.

The results for all of the formulations containing the dosage levels of example 4 or greater (this includes the compositions of examples 2, 3, 4 and 11), the average results are: poor-13.75%; good-31.25%; and excellent-55.00%.

The results for all formulations containing less than the dosage level of Example 4 (this includes examples 1, 5, 6, 7, 8, 9 and 10) are poor-26.24%; good-57.45%; and excellent 16.31%.

It is readily apparent that all of the formulations, in the varying amounts which are illustrated in the eleven examples, produce at least seventy percent good to excellent results in the reduction of snoring. The most effective formulations (that is, those which include amounts of each ingredient equal to or in excess of the compositions used in Example 4) produced 86.25% good to excellent results.

In all of the tests of the above examples, there was found to be no correlation with gender or age. Also, there was no correlation with weight, as long as the dosage was varied by weight, as described above, that is one capsule or tablet for up to 125 pounds of body weight, two capsules for 125 pounds to 220 pounds of body weight and three capsules for body weight of over 220 pounds.

During testing of the various formulations described in the above examples, out of the total number of patients tested, 112 of the group also complained of allergy and sinus problems prior to undertaking the tests. The allergic symptoms primarily consisted of upper airway congestion, respiratory tract drainage, coughs, nasal discharge, and sneezing. The sinus symptoms were principally nasal discharge, sneezing, coughing, a sensation of fullness in the face and/or head and headaches. These patients were provided with additional capsules or tablets, as described above, which were taken on a dosage schedule of one to two capsules or tablets every six to eight hours, as needed. In reporting the results of relief from sinus or allergic symptoms, the results were reported as poor being 0% to 50% improvement; good being 50% to 75% improvement; and excellent being 75% to 100% improvement. The formulation used in each test group corresponded to those used in the above eleven examples for the snoring study. In the following, the designation "GROUP" is used to differentiate the allergy/sinus results from the examples explained above for the snoring study. Each of the groups listed below, however, corresponds to the same numbered snoring "Example" designations; and the subjects which took part in the sinus/allergy testing within each of the groups also were included within the larger corresponding snoring test examples. The compositions of the tablets or capsules adminstered to the subjects in the groups designated below are identical to the compositions of the tablets or capsules provided by the same numbered examples in the snoring study previously explained. As a consequence, the composition of the tablets will not be repeated here, since it is redundant. For example, the tablet combination of "EXAMPLE 9" given in the above snoring study is the same tablet composition provided in "GROUP 9" below for the sinus/allergy testing. The following eleven groups for the sinus/allergy testing and the results of the testing are provided:

GROUP 1

Subjects

Six subjects, including five women and one man, were tested. The age range of the subjects was 24 years to 67 years.

| Results | | |
|---|---|---|
| POOR - 45% | GOOD - 45% | EXCELLENT - 10% |

GROUP 2

Subjects

A total of fourteen subjects, including two women and twelve men were tested. The age range of the subjects was 18 years to 56 years.

| Results | | |
|---|---|---|
| POOR - 15% | GOOD - 35% | EXCELLENT - 50% |

GROUP 3

Subjects

A total of eleven subjects, including five women and six men, were tested. The age range was 18 years to 69 years.

| Results | | |
|---|---|---|
| POOR - 10% | GOOD - 30% | EXCELLENT - 60% |

GROUP 4

Subjects

A total of twelve subjects, including five women and seven men, were tested. The age range was 23 years to 62 years.

| Results | | |
|---|---|---|
| POOR - 15% | GOOD - 40% | EXCELLENT - 45% |

GROUP 5

Subjects

A total of ten subjects, including seven women and three men, were tested. The age range of the subjects was 31 years to 52 years.

| Results | | |
|---|---|---|
| POOR - 30% | GOOD - 50% | EXCELLENT - 20% |

GROUP 6

Subjects

A total of eleven subjects, including two women and nine men, were tested. The age range of the subjects was 23 years to 60 years.

| Results | | |
|---|---|---|
| POOR - 30% | GOOD - 55% | EXCELLENT - 15% |

GROUP 7

Subjects

A total of fourteen subjects, including ten women and four men, were tested. The age range was 25 years to 67 years.

| Results | | |
|---|---|---|
| POOR - 30% | GOOD - 50% | EXCELLENT - 20% |

GROUP 8

Subjects

A total of nine subjects, including three women and six men, were tested. The age range of the subjects was 26 years to 64 years.

| Results | | |
|---|---|---|
| POOR - 30% | GOOD - 45% | EXCELLENT - 25% |

GROUP 9

Subjects

A total of nine subjects, including five women and four men, were tested. The age range of the subjects was 23 years to 70

| Results | | |
|---|---|---|
| POOR - 30% | GOOD - 50% | EXCELLENT - 20% |

GROUP 10

Subjects

A total of eight subjects, including four women and four men, were tested. The age range of the subjects was 22 years to 67 years.

| Results | | |
|---|---|---|
| POOR - 25% | GOOD - 55% | EXCELLENT - 20% |

GROUP 11

Subjects

A total of eight subjects, including two women and six men, were tested. The age range of the subjects was 22 years to 50 years.

| Results | | |
|---|---|---|
| POOR - 10% | GOOD - 30% | EXCELLENT - 60% |

For the above subjects who complained of allergy or sinus problems prior to the tests, the overall results, in reduction in or relieving of upper respiratory congestion from sinus or allergy conditions for the entire range of formuation, produced results of poor-23.6%; good-43.8%;i and excellent-32.6%.

The results for all formulations containing the dosage levels of Group 4 (Example 4) or greater (this includes the compositions of Examples/Groups 2, 3, 4 and 11), the average results are: poor-12.9%; good-34.2%; and excellent-52.9%.

The results for all formulations containing less than the dosage levels of Example 4 (Group 4), which includes Examples/Groups 1, 5, 6, 7, 8, 9 and 10, are: poor-30.7%; good-50.3%; and excellent-19%.

The conclusions which may be drawn from these studies for sinus/allergy reduction are that all formulations produced good to excellent results in at least 70% of the patients. The most effective formulations contain dosage of each ingredient equal to or in excess of the formulation used in Example 4/Group 4, producing 87.1% good to excellent results. From the evaluation of the tests, no correlation with gender, age or weight based on the dosage range listed above was found.

Although various ranges of formulation have been described above, various changes and modifications may be made by those skilled in the art for performing substantially the same function, in substantially the same way, to achieve substantially the same result, without departing from the true scope of the invention as defined in the appended claims.

What is claimed:

1. A composition for reducing snoring and alleviating respiratory problems due to an interference with the passage of air through the upper respiratory system including in combination:

between 5,000 and 40,000 hemoglobin units (HU) of protease between 500 and 20,000 dextrizing units (DU) of amylase, between 10 and 1,600 lipase units (LU) of lipase, between 50 and 10,000 cellulase units (CU) of cellulase, between 25 and 250 milligrams (mg) of acerola, and between 25 to 250 milligrams (mg) of yellowdock in a carrier.

2. The composition according to claim 1 wherein said composition comprises at least 5,000 HU of protease, 2,000 DU of amylase, 40 LU of lipase, 200 CU of cellulase, 75 mg of acerola, and 100 mg of yellowdock.

3. The composition according to claim 2 wherein said carrier is a natural fiber carrier.

4. The composition according to claim 3 wherein said carrier comprises beet plant fiber.

5. The composition according to claim 3 wherein the quantity of natural fiber carrier is a quantity sufficient for an orally administered tablet.

6. A method for reducing snoring and alleviating respiratory problems due to an interference of the passage of air through the upper respiratory system by administering the composition of claim 5 comprising the step of orally swallowing at least one tablet forty-five to sixty minutes before bedtime.

7. The method according to claim 6 wherein the number of tablets swallowed is based on weight, with one tablet for weight up to 125 pounds, two tablets for a weight between 125 pounds and 220 pounds, and three tablets for body weight over 220 pounds.

8. The composition according to claim 3 wherein the quantity of said natural fiber carrier is a quantity sufficient for an orally administered capsule.

9. A method for reducing snoring and alleviating respiratory problems due to an interference of the passage of air through the upper respiratory system by administering the composition of claim 8 comprising the step of orally swallowing at least one capsule forty-five to sixty minutes before bedtime.

10. The method according to claim 9 wherein the number of capsules is based on weight, with one capsule for weight up to 125 pounds, two capsules for a weight between 125 pounds and 220 pounds, and three capsules for body weight over 220 pounds.

11. The composition according to claim 4 wherein the quantity of natural fiber carrier is a quantity sufficient for an orally administered tablet.

12. A method for reducing snoring and alleviating respiratory problems due to an interference of the passage of air through the upper respiratory system by administering the composition of claim 11 comprising the step of orally swallowing at least one tablet forty-five to sixty minutes before bedtime.

13. The method according to claim 12 wherein the number of tablets swallowed is based on weight, with one tablet for weight up to 125 pounds, two tablets for a weight between 125 pounds and 220 pounds, and three tablets for body weight over 220 pounds.

14. The composition according to claim 4 wherein the quantity of said natural fiber carrier is a quantity sufficient for an orally administered capsule.

15. A method for reducing snoring and alleviating respiratory problems due to an interference of the passage of air through the upper respiratory system by administering the composition of claim 14 comprising the step of orally swallowing at least one capsule forty-five to sixty minutes before bedtime.

16. The method according to claim 15 wherein the number of capsules is based on weight, with one capsule for weight up to 125 pounds, two capsules for a weight between 125 pounds and 220 pounds, and three capsules for body weight over 220 pounds.

17. The composition according to claim 1 wherein said carrier is a natural fiber carrier.

18. The composition according to claim 1 wherein said carrier comprises a liquid carrier.

19. The composition according to claim 18 wherein said liquid carrier comprises a flavored liquid carrier.

* * * * *